United States Patent [19]

Goldstein et al.

[11] Patent Number: 4,980,357

[45] Date of Patent: Dec. 25, 1990

[54] AZOLIDINEDIONE DERIVATIVES

[75] Inventors: Steven W. Goldstein; Reinhard Sarges, both of Mystic, Conn.

[73] Assignee: Pfizer Inc., New York, N.Y.

[21] Appl. No.: 474,722

[22] Filed: Mar. 1, 1990

[51] Int. Cl.$^5$ .................. C07D 513/20; C07D 498/20; A61K 31/395

[52] U.S. Cl. ........................................ 514/278; 546/15

[58] Field of Search ........................... 546/15; 514/278

[56] References Cited

U.S. PATENT DOCUMENTS

| 3,821,383 | 9/1974 | Sestanj et al. | 424/258 |
| 4,117,230 | 9/1978 | Sarges | 548/309 |
| 4,130,714 | 12/1978 | Sarges | 548/309 |

FOREIGN PATENT DOCUMENTS

| 0553839 | 5/1986 | Australia | 548/308 |
| 2080304 | 2/1982 | United Kingdom | 548/309 |

*Primary Examiner*—Robert T. Bond
*Attorney, Agent, or Firm*—Peter C. Richardson; Paul H. Ginsburg

[57] ABSTRACT

A series of novel spiro-deteroazolones derived from a 2,3-dihydropryrano[2,3-b]pyridine ring system have been prepared, including their pharmaceutically acceptable salts. These compounds are useful in therapy as aldose reductase inhibitors for the control of certain chronic diabetic complications. Typical member compounds include spiro-imides, spiro-oxazolidinediones, spiro-thiazolidinediones and spiro-imidazolidinediones derived from the aforesaid ring system. (4'S) (2'R)-6'-Chloro-2',3'-dihydro-2'-methyl-spiro-[imidazolidine-4,4'-4'H-pyrano[2,3-b]pyridine]-2,5-dione represents a typical and preferred member compound. Methods for preparing all these compounds from known starting materials are provided.

29 Claims, No Drawings

AZOLIDINEDIONE DERIVATIVES

TECHNICAL FIELD

This invention relates to new azolidinedione derivatives of interest to those in the field of medicinal chemistry and chemotherapy. More particularly, it is concerned with a series of spiro-heteroazolone compounds that are derived from a 2,3-dihydropyrano[2,3-b]pyridine ring system. These novel compounds are useful in therapy for the control of certain chronic complications arising from diabetes mellitus (e.g., diabetic cataracts, retinopathy and neuropathy).

BACKGROUND ART

Past attempts to obtain new and better oral antidiabetic agents have, for the most part, involved an endeavor to synthesize new compounds that lower blood sugar levels. More recently, several studies have been conducted concerning the effect of various organic compounds in preventing or arresting certain chronic complications of diabetes, such as diabetic cataracts, neuropathy and retinopathy, etc. For instance, K. Sestanj et al. in U.S. Pat. No. 3,821,383 discloses that certain aldose reductase inhibitors like 1,3-dioxo-1H-benz[d,e]isoquinoline-2(3H)-acetic acid and some closely-related derivatives thereof are useful for these purposes even though they are not known to be hypoglycemic. These compounds function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of diabetic subjects are prevented or reduced. As a result, these compounds control certain chronic diabetic complications, including those of an ocular nature, since it is already known in the art that the presence of polyols in the lens of the eye leads to cataract formation and concomitant loss of lens clarity.

DISCLOSURE OF THE INVENTION

The present invention relates to novel spiro-heteroazolone compounds useful as aldose reductase inhibitors for the control of certain chronic complications arising in a diabetic subject. More specifically, the novel compounds of this invention are selected from the group consisting of spiro-imides, spiro-oxazolidinediones, spiro-thiazolidinediones and spiro-imidazolidinediones of the formula:

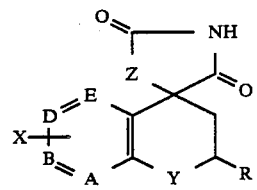

and the base salts thereof with pharmacologically acceptable cations, wherein X is hydrogen, fluorine, chlorine, bromine, nitro, trifluoromethyl, $C_1$–$C_4$ alkyl, $C_1$–$C_4$ alkoxy or $C_1$–$C_4$ alkylthio; Z is methylene, oxygen, sulfur or imino; Y is oxygen or sulfur; and R is hydrogen or $C_1$–$C_4$ alkyl, and —A=B—D=E— represents —N=CH—CH=CH—, —CH=N—CH=CH—, —CH=CH—N=CH— or —CH=CH—CH=N—, or an N-oxide derivative thereof. These novel compounds are aldose reductase inhibitors and therefore, possess the ability to reduce or inhibit sorbitol formation in the lens, retina, kidney and peripheral nerves of diabetic subjects.

One group of compounds of the present invention of particular interest is that of the general structural formula wherein X, Y and R are each defined as aforesaid, Z is imino, and —A=B—D=E— represents —N=CH—CH=CH—. Preferred compounds within this group include those where X is hydrogen, fluorine, chlorine or bromine, Y is oxygen and R is hydrogen or methyl. Especially preferred members include those where X is chlorine or bromine and R is methyl.

Another group of compounds of the present invention of interest is that of the aforesaid structural formula wherein X is hydrogen, fluorine, chlorine or bromine, Y is oxygen, Z is imino, R is defined as aforesaid and —A=B—D=E— represents the N-oxide derivatives of —N=CH—CH=CH—. Preferred compounds within this group include those where X is chlorine and R is hydrogen or methyl.

Of special interest are such typical and preferred member compounds of the invention as (+)-cis-6'-chloro-2',3'-dihydro-2'-methyl-spiro-[imidazolidine-4,4'-4'H-pyrano[2,3-b]pyridine]-2,5-dione (where cis means that 2'-methyl and 4'—NH are on the same side of the pyran ring), (+)-trans-6'-chloro-2',3'-dihydro-2'-methyl-spiro-[imidazolidine-4,4'-4'H-pyrano[2,3-b]pyridine]-2,5-dione (where trans means that 2'-methyl and 4'—NH are on opposite sides of the pyran ring), (+)-cis-6'-fluoro-2',3'-dihydro-2'-methyl-spiro-[imidazolidine-4,4'-4'H-pyrano[2,3-b]pyridine]-2,5-dione, (+)-cis-6'-bromo-2',3'-dihydro-2'-methyl-spiro-[imidazolidine-4,4'-4'H-pyrano[2,3-b]pyridine]-2,5-dione, (4'S)(2'R)-6'-chloro-2',3'-dihydro-2'-methyl-spiro-[imidazolidine-4,4'-4'H-pyrano[2,3-b]-pyridine]-2,5-dione and (4'S)(2'R)-6'-chloro-2',3'-dihydro-2'-methyl-spiro-[imidazolidine-4,4'-4'H-pyrano-[2,3-b]pyridine]-2,5-dione-8'-oxide. These key compounds are potent aldose reductase inhibitors, in addition to being particularly effective in lowering sorbitol levels in the sciatic nerve, retina and lens of diabetic subjects.

DETAILED DESCRIPTION

In accordance with the process employed for preparing the novel compounds of this invention of the general structural formula I wherein Z is imino, an appropriately substituted carbonyl compound of the formula:

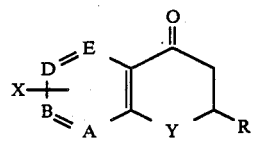

wherein X, Y and R are each as previously defined, is condensed with an alkali metal cyanide (e.g. sodium cyanide or potassium cyanide) and ammonium carbonate to form the desired spiro-imidazolidinedione final product of the structural formula previously indicated. This particular reaction is normally carried out in the presence of a reaction-inert polar organic solvent medium in which both the reactants and reagents are mutually miscible. Preferred organic solvents for use in this connection include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylacetamide, etc., in addition to the corresponding unsubstituted alkanoamides having from one to four carbon atoms such as formamide, acetamide and the like. In general, the reaction is conducted at a temperature that is in the range of from about 25° C. up to about 150° C. for a period of about two hours to about four days. Although the amount of reactant and reagents employed in the reaction can vary to some extent, it is preferable to employ at least a slight molar excess of both the alkali metal cyanide and ammonium carbonate reagents with respect to the carbonyl ring compound starting material in order to effect maximum yield. Upon completion of the reaction, the desired product is normally isolated in a conventional manner, e.g., by first diluting the reaction mixture with ice water, followed by acidification to afford the desired spiro-imidazolidinedione compound in a form which is readily-recoverable from the reaction mixture. Further purification can then be carried out by such means as silica gel column chromatography and the like, in addition to standard recrystallization techniques.

Compounds of the invention of structural formula I wherein Z is methylene (i.e., spiro-imides) can be prepared by subjecting the appropriately substituted carbonyl ring compound of structural formula II to the series of reactions described by J. L. Belletire et al., in U.S. Pat. No. 4,307,108, whereby the carbonyl ring compound is condensed with a lower alkyl α-cyanoacetate to give the corresponding cyano-ylidene acetate, which is then treated with potassium cyanide to form the corresponding dicyano compound followed by acid hydrolysis in a conventional manner to yield the corresponding dicarboxylic acid and finally heat treatment of the latter compound with concentrated ammonia at about 200°–300° C., until at least all the volatile material is removed from the mixture and the resultant product forms a homogeneous mass, to ultimately yield the desired spiro-imide final product of the structural formula previously indicated.

Compounds of the invention of structural formula I wherein Z is oxygen (i.e., spiro-oxazolidinediones) or sulfur (i.e. spiro-thiazolidinediones) can be prepared by subjecting the appropriately substituted carbonyl ring compound of structural formula II to the series of reactions described by R. C. Schnur in U.S. Pat. Nos. 4,226,875 and 4,267,342. For instance, in one procedure to prepare a compound where Z is oxygen, a carbon atoms and is preferably methyl, to form the corresponding cyano trialkylsiloxy derivative. The reaction is conducted in the presence of a Lewis acid catalyst, such as zinc halide, aluminum halide or boron trifluoride, with zinc iodide being a preferred catalyst. Temperatures in the range of about 0° C. to about 50° C. are generally employed, preferably about 0° C. to 20° C., in an inert organic solvent, typically an ether such as diethyl ether, dimethoxyethane, tetrahydrofuran, dioxane and the like, or a halohydrocarbon such as methylene chloride, chloroform and similar solvents. The resulting cyano trialkylsilyloxy derivative is then converted to an alkyl-hydroxycarboximidate derivative by reaction with an acid in an alcohol solvent medium. Suitable acids include hydrogen halides, especially hydrogen chloride. The alcohol may be either a lower alkanol of 1 to 4 carbon atoms, benzyl alcohol or a substituted benzyl alcohol, the substituent including chloro, bromo, fluoro, hydroxy, alkyl of 1 to 3 carbon atoms and alkoxy of 1 to 3 carbon atoms. The reaction is generally conducted at temperatures in the range of about −10° C. to about 25° C., preferably at about 0° C. to 10° C.

The hydroxy carboximidate derivative may then be converted directly to the desired spiro-oxazolidin-2,4-dione by a number of methods. In all cases, a spiro-4-alkoxy-oxazolin-2-one is an intermediate and can, if desired, be isolated from the reaction mixture. However, it is generally preferred to convert directly without such isolation of the intermediate. The hydroxy carboximidate may be reacted with phosgene in the presence of a base such as triethylamine, or other trialkylamines having from 1 to 4 carbon atoms in each dimethoxyethane, dioxane and the like. The phosgene is generally bubbled through the reaction solution at a temperature of about −10° C. to about 10° C., for about 5 to 15 minutes and the solution is subsequently stirred at about 20° C. to 50° C., preferably at about 25° C. for about 12 to 48 hours, when the spiro-oxazolin-2-one is predominantly formed. This intermediate may then be converted to the desired spiro-oxazolidin-2,4-dione either by a further perfusion of phosgene at about −10° C. to about 10° C. for about 15 to 75 minutes, followed by stirring at room temperature for a further period of about 12 to 48 hours. Alternatively, an alkali metal carbonate, such as potassium or sodium carbonate, or ammonium carbonate can be added to a solution of the intermediate in, for example, aqueous tetrahydrofuran, and stirred at a temperature of about 15° C. to about 50° C., preferably at about 25° C. for a period of about six to 24 hours to form the desired spiro-oxazolidin-2,4-dione.

The desired spiro-oxazolidin-2,4-dione can also be prepared from the hydroxy carboximidate derivative by reaction with an alkyl haloformate, where the alkyl group is of 1 to 4 carbon atoms, a preferred reagent being ethyl chloroformate. The reaction is generally conducted by stirring the hydroxy carboximidate intermediate together with the alkyl haloformate in an inert solvent, such as pyridine, at a temperature of −10° C. to about 15° C., preferably at 0° C. for a period of 30 minutes to about two hours, followed by heating the solution to a higher temperature, say at about 50° C. to about 150° C., preferably about 90° C. to 120° C., for example, to reflux temperature in pyridine, for about 2 to about 6 hours If desired the spiro-oxazolidin-2-one intermediate can be isolated from the initial reaction mixture after heating the solution for relatively shorter periods, e.g., about one hour.

The spiro-oxazolidin-2,4-diones can also be prepared from the hydroxy carboximidate derivative by reaction with 1,1′-carbonyl-diimidazole, the reaction being generally conducted at a temperature of about 50° C. to 150° C., preferably about 80° C. to 110° C., neat or in an inert organic solvent such as dioxane, tetrahydroforan, dimethoxyethane, diethyl ether and the like, for a period of about 12 to 36 hours. If desired, the intermediate spiro-oxazolin-2-one can be obtained by heating for only a relatively short period of time, for example, about 30 minutes to about 90 minutes.

When Z is sulfur, the compounds of structural formula I can be prepared by taking advantage of the hydroxy carboximidate derivative as previously discussed. These are converted to chlorocarboximidate derivative by heating with thionyl chloride at between about 35°

C. and the reflux temperature of about 79° C. for 1–3 hours, preferably about two hours. The resulting chlorocarboximate derivatives are reacted with thiourea in a refluxing alkanol of 1–4 carbons, preferably ethanol, for about 15–90 minutes, preferably 30 minutes, followed by a brief aqueous hydrolysis either during column chromatography on acidic silica gel, or in aqueous tetrahydrofuran or dioxane containing about 1–6N hydrochloric acid at about 0°–60° C., and preferably at about 25° C.

As regards compounds of the invention of structural formula I wherein X is hydroxy, these can readily be prepared from the corresponding compounds where X is methoxy by simply dealkylating same in accordance with standard techniques well known to those skilled in the art. For instance, the use of boron tribromide in this connection readily converts a 6-methoxy substituted compound of the invention to the corresponding 6-hydroxy compound. Moreover, certain compounds of the invention having a ring substituent (X) which is lower alkoxy of more than one carbon atom can alternatively be prepared from the corresponding methoxy compounds by first converting same to the corresponding hydroxy derivatives and then alkylating the latter with, for example, ethyl iodide or isopropyl bromide in a manner well known to those skilled in the art. Moreover, certain compounds of the invention having a ring substituent (X) which is halogen (as previously defined) or nitro may alternatively be prepared from the corresponding unsubstituted compounds wherein X is hydrogen by means of direct halogenation or nitration techniques that are respectively well known to those skilled in the field of synthetic organic chemistry. On the other hand, a halogen-substituted compound prepared according to the principal process of the invention, such as a 6-chloro compound, can easily be converted to the corresponding unsubstituted (i.e., 6-dehalo) compound by means of standard techniques well-known to those skilled in the art for effecting hydrogenolysis, 0538 e.g., catalytic hydrogenation. In this way, (+)-cis-6'-chloro-2',3'-dihydro-2'-methyl-spiro-[imidazolidine-4,4'-4'H-pyrano[2,3-b]pyridine]-2,5-dione is readily converted to the corresponding 6-deschloro compound.

Compounds of the invention which are N-oxide derivatives of the parent compounds can be prepared by simply subjecting the latter to well-known oxidative procedures which are required for effecting such a conversion from the parent compound, e.g., oxidation via 30% hydrogen peroxide or benzoyl peroxide etc. In one such procedure, oxidation if preferably effected by using 30% aqueous hydrogen perioxide in an acidic solvent such as that provided by acetic acid at a temperature ranging between about 0°–100° C., and preferably at about 80°–90° C. for a period of approximately 16 hours.

The ketone starting materials (i.e., carbonyl ring compounds of structural formula II) required for preparing the desired final products of structural formula I in the overall process of this invention are, for the most part, new compounds (i.e., where X is other then hydrogen), which are conveniently prepared by a multi-step series of reactions starting from readily available organic materials. For instance, novel 2,3-dihydro-4H-pyrano[2,3-b]pyridine-4-one compounds of the formula II wherein Y is oxygen are prepared in an elegant fashion from the known 2-methoxynicotinic acid via a multi-step series of reactions that is described in the experimental section of the instant specification (e.g., see Preparations A–Y).

In a similar manner, the corresponding 2,3-dihydro-4H-thiopyrano(2,3-b)pyridin-4-ones of the formula II wherein Y is sulfur can be prepared from 2-methylthionicotinic acid.

Inasmuch as the spiro-heteroazolone compounds of this invention all possess at least one asymmetric center, they are capable of existing in various stereoisomeric forms. For instance, compounds of the invention of structural formula I where R is hydrogen possess one asymmetric center, whereas those where R is $C_1$–$C_4$ alkyl possess two asymmetric centers. Hence, the compounds can exist in separated (+)- and (−)-optically active forms, as well as in racemic or (±)-mixtures thereof, and in the case of those compounds with two asymmetric centers, they can additionally exist as diastereomers with respective optical isomers thereof. The present invention is meant to include all such forms within its scope. For instance, the diastereomers can be separated by methods well known to those skilled in the art, e.g., by fractional crystallization and the like, while the optically active isomers can be obtained by simply resolving the racemates via standard techniques that will hereinafter be more fully described in the experimental section of the instant specification (see Examples 10–13 in this regard).

The chemical bases which are used as reagents in this invention to prepare the aforementioned pharmaceutically acceptable base salts are those which form non-toxic base salts with the herein described spiro-heteroazolone compounds such as (4'S)(2'R)-6'-chloro-2',3'-dihydro-2'-methyl-spiro-[imidazolidine-4,4'-4'H-pyrano[2,3-b]pyridine]-2,5-dione, for example. These particular non-toxic base salts include those derived from such pharmacologically acceptable cations as sodium, potassium, calcium and magnesium, etc. These salts can easily be prepared by simply treating the aforementioned spiro-heteroazolone compounds with an aqueous solution of the desired pharmacologically acceptable cation, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

As previously indicated, the spiro-heteroazolone compounds of this invention are readily adapted to therapeutic use as aldose reductase inhibitors for the control of certain chronic diabetic complications, in view of their ability to reduce lens and peripheral nerve sorbitol levels in diabetic subjects to a statistically significant degree. For instance, (4'S)(2'R)-6'-chloro-2',3'-dihydro-2'-methyl-spiro-[imidazolidine-4,4'-4'H-pyrano[2,3-b]pyridine]-2,5-dione, a typical and preferred agent of the present invention, has been found to inhibit the formation of sorbitol levels in both the sciatic nerve and lens of diabetic rats to a significantly high degree when given by the oral route of administration at dose levels ranging from 0.1–10.0 mg./kg. Furthermore, the herein described compounds of this invention can be administered by either the oral, topical or parenteral routes of administration. In general, these compounds are ordinarily administered in dosages ranging from about 0.05 mg. to about 10 mg. per kg. of body weight per day, although variations will necessarily occur depending upon the weight and condition of the subject being treated and the particular route of administration chosen.

These compounds may be administered either alone or in combination with pharmaceutically acceptable carriers by any of the various routes previously indicated, and such administration can be carried out in either single or multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. In general, the compounds of the invention will be present in such dosage forms at concentration levels ranging from about 0.5% to about 90% by weight of the total composition to provide the desired unit dosage.

For oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various combinations thereof.

For parenteral administration, solutions of these spiro-heteroazolones in sesame or peanut oil or in aqueous propylene glycol or N,N-dimethylformamide may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection. In this connection, the sterile aqueous media employed are all readily obtainable by standard techniques well-known to those skilled in the art. Additionally, it is also possible to administer the aforesaid spiro-heteroazolone compounds topically via an appropriate ophthalmic solution (0.5-2.0%) applied dropwise to the eye.

The activity of the compounds of the present invention, as agents for the control of chronic diabetic complications, is determined by their ability to successfully pass one or more of the following standard biological or pharmacological tests, viz., (1) measuring their ability to inhibit the enzyme activity of isolated aldose reductase; (2) measuring their ability to reduce or inhibit sorbitol accumulation in the sciatic nerve and lens of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

PREPARATION A

A stirred slurry consisting of 35 g. (0.22 mole) of 2-chloronicotinic acid (available from Lonza Inc. of Fair Lawn, N.J.) in 400 ml. of methanol was treated with 25.4 g. (0.47 mole) of sodium methylate, which was added thereto in a portionwise manner. Stirring was then continued until a clear solution was obtained. At this point, the liquid reaction mixture was transferred to a steel autoclave and heated at 125° C. for a period approximately 16 hours (i.e., overnight). Upon completion of this step, the resulting reaction mixture was cooled to room temperature (~20° C.), filtered and the filter cake thus obtained was washed with methanol. The combined organic filtrate and methanol washings were then concentrated in vacuo to give a white solid material, which was subsequently dissolved in water. The latter aqueous solution was then adjusted to pH 3 with the aid of 6N hydrochloric acid and immediately filtered to remove (i.e., recover) the precipitated solid product, which was thereafter air dried (to constant weight) for a period of approximately 16 hours (i.e., overnight). In this manner, there were ultimately obtained 21.8 g. (64%) of pure 2-methoxynicotinic acid, m.p. 147°–148° C. (literature m.p. 144°–146° C., according to D. E. Kuhla et al., in U.S. Pat. No. 3,879,403). The pure product was further characterized by means of nuclear magnetic resonance data.

PREPARATION B

In a reaction flask equipped with a mechanical stirrer and dry ice condenser, there were placed 25.5 g. (0.166 mole) of 2-methoxynicotinic acid (the product of Preparation A) and 1500 ml. of water. Stirring was then commenced and chlorine gas was bubbled into the resultant slurry until saturation of same was complete with respect to said gas. This step required a period of 30 minutes. At the end of this time, the reaction mixture was allowed to stir at room temperature (~20° C.) for a period of approximately 16 hours (i.e., overnight) and then was filtered to remove crude product. The latter material was then washed with water and air dried, prior to being taken up in chloroform. The chloroform solution was then washed once with saturated brine and dried over anhydrous magnesium sulfate. After removal of the drying agent by means of filtration and the solvent by means of evaporation under reduced pressure, there were ultimately obtained 26.2 g. (84%) of pure 5-chloro-2-methoxynicotinic acid in the form of a white solid material melting at 149°–151° C. (literature m.p. 149°–150° C., according to D. E. Kuhla et al. in U.S. Pat. No. 3,879,403). The pure product was further characterized by means of nuclear magnetic resonance data.

PREPARATION C

A 217 g. (1.42 mole) sample of 2-methoxynicotinic acid (the product of Preparation A) was added portionwise to 2.5 liters of well-stirred 5% aqueous sodium hypochlorite solution (Clorox) at 10° C., with sufficient cooling being maintained throughout the course of the addition step to keep the temperature of the reaction mixture below 28° C. Upon completion of this step, the resulting reaction mixture was allowed to stir at room temperature (~20° C.) for a period of approximately 16 hours (i.e., overnight) and then acidified to pH 2.0 with concentrated hydrochloric acid. The precipitated solid product was then collected by means of suction filtration and thereafter triturated with two-500 ml. portions of hexanes, followed by drying under a high vacuum to ultimately afford 201 g. (75%) of pure 5-chloro-2-methoxynicotinic acid. This product was identical in every respect with the product of Preparation B, as particularly attested to by nuclear magnetic resonance data.

PREPARATION D

A mixture consisting of 100 g. (0.533 mole) of 5-chloro-2-methoxynicotinic acid (the product of Preparation C) suspended in 500 ml. of methanol containing ca. 3.0 ml. of concentrated sulfuric acid was stirred and heated to reflux for a period of three hours in a 1-liter round-bottomed reaction flask. Upon completion of this step, the reaction mixture was cooled to room temperature (~20° C.) with stirring and then allowed to stir overnight at ambient temperatures for a period of approximately 16 hours. The precipitated crystalline product was recovered from the reaction mixture by means of suction filtration and the collected crystals thereafter washed with fresh methanol to ultimately afford 59.5 g. (55%) of pure methyl 5-chloro-2-methoxynicotinate, m.p. 86°–87° C. A second crop consisting of 18.4 g. (17%) of the same pure product was obtained from the mother liquor. The total yield of pure product was 72% of the theoretical value. The pure product was further characterized by means of nuclear magnetic resonance data.

PREPARATION E

In a three-necked, round-bottomed reaction flask equipped with mechanical stirrer and nitrogen-inlet tube, there were placed 63.0 g..(0.312 mole) of methyl 5-chloro-2-methoxynicotinate (the product of Preparation D) in 300 ml. of dry tetrahydrofuran while under a dry nitrogen atmosphere, followed by the addition thereto of 27.9 ml. (0.373 mole) of acetone and 20.1 g. (0.373 mole) of sodium methoxide with constant agitation being maintained throughout the course of the entire addition step. The resulting reaction mixture was then stirred at room temperature (~20° C.) for a period of ca. 20 hours, followed by filtration through a 25–50 μm. fitted glass filter funnel. After washing the filtered product with 100 ml. of ethyl acetate and vacuum drying to constant weight, there were obtained 72.65 g. (92%) of 3-acetonylcarbonyl-5-chloro-2-methoxypyridine as the sodium salt in the form of a tan-white non-hygroscopic powder, m.p. >250° C.

PREPARATION F

A solution consisting of 44.5 g. (0.177 mole) of the sodium salt of 3-acetonylcarbonyl-5-chloro-2-methoxypyridine (the product of Preparation E) dissolved in 650 ml. of glacial acetic acid was placed in a reaction flask and heated to 100° C. by means of an oil bath at 115° C. At this point, 65 ml. of 48% hydrobromic acid was added to the hot solution and the temperature of the oil bath was raised from 115° C. to 130° C. The reaction mixture was then stirred for a period of 15 minutes, while the height of the oil bath was adjusted so as to keep the internal temperature of the reaction mixture at 100° C. throughout the final heating step. Upon completion of this step, the reaction mixture was cooled rapidly in an ice bath to 24° C. and then poured into 2-liters of ice water. The resulting aqueous solution was next extracted with three-250 ml. portions of methylene chloride, and the combined organic layers were subsequently washed with two-250 ml. portions of water and then with 2% aqueous sodium hydroxide solution (using 250 ml. portions) until the water layers became basic. After drying the washed organic layer over anhydrous magnesium sulfate and filtering to remove the drying agent, the product was recovered from the clear filtrate by concentrating same in vacuo to ultimately yield 19.3 g. (56%) of pure 6-chloro-2-methyl-4H-pyrano[2,3-b]pyridin-4-one. The pure product was characterized by means of nuclear magnetic resonance data.

PREPARATION G

A stirred mixture consisting of 15.0 g. (0.0767 mole) of 6-chloro-2-methyl-4H-pyrano[2,3-b]pyridin-4-one (the product of Preparation F) suspended in 250 ml. of tetrahydrofuran was cooled to −72° C. by means of a dry ice bath at −78° C. To the cooled mixture, there were then added 3.06 g. (0.080 mole) of lithium aluminum hydride portionwise during the course of a 10-minute period. Upon completion of this step, the resulting mixture was stirred at −78° C. (bath temperature) for a period of 14 hours. At this point, 19.5 ml. of glacial acetic acid (4.44 equivalents) dissolved in 25 ml. of tetrahydrofuran were added to the stirred mixture over a one-hour period in such a manner as to keep the internal reaction temperature below −45° C. throughout the course of the addition step. The spent reaction mixture was then allowed to recool to −70° C. before being poured into one liter of cold water and thereafter extracted with three-300 ml. portions of diethyl ether. After successively washing the combined organic extracts with water (500 ml.), 2% aqueous sodium hydroxide solution (200 ml.) and water again (2×200 ml.), the organic solution was dried over anhydrous magnesium sulfate and filtered. Evaporation of the clear filtrate under reduced pressure then gave 7.51 g. (50%) of pure 6-chloro-2,3-dihydro-2-methyl-4H-pyrano[2,3-b]pyridin-4-one, m.p. 84°–86° C. This pure product was further characterized by means of mass spectroscopy and nuclear magnetic resonance data.

PREPARATION H

In a dry 2-liter, three-necked round-bottomed reaction flask equipped with thermometer, mechanical stirrer and dropping funnel, there were placed 25.13 g. (0.128 mole) of 6-chloro-2-methyl-4H-pyrano[2,3-b]-pyridin-4-one (the product of Preparation F). A solution consisting of 615 ml. of methylene chloride and 154 ml. of tetrahydrofuran was then added via the dropping funnel. The resulting solution was stirred and then cooled in a dry ice/acetone bath to give an internal temperature reading of ca. −70° C. At this point, 166 ml. of a 1M solution of diisobutylaluminum hydride (0.166 mole) in toluene were gradually added to the chilled reaction solution through the dropping funnel. This step required a period of 20 minutes, during which time a slight exothermic rise (ca. 5° C.) in the reaction mixture was noted. After stirring for a period of four hours at a bath temperature of −78° C., the reaction was quenched by the addition of 15.04 g. (0.250 mole) of glacial acetic acid dissolved in 15 ml. of tetrahydrofuran. After allowing the spent reaction mixture to gradually warm to room temperature (~20° C.), it was poured into one liter of water and the resulting aqueous layer acidified to pH 2.0 by the addition thereto of dilute hydrochloric acid. The two layers were then separated and the separated aqueous layer was thereafter extracted with 500 ml. of methylene chloride. The combined organic layers were then dried over anhydrous magnesium sulfate and filtered, and the resulting filtrate subsequently evaporated in vacuo to give 23.42 g. (93%) of pure 6-chloro-2,3-dihydro-2-methyl-4H-pyrano[2,3-b]pyridin-4-one in the form of a light brown solid. This product was identical in every respect with the product of Preparation G, as particularly attested to by nuclear magnetic resonance data.

PREPARATION I

In a 1-liter round-bottomed reaction flask containing a well-stirred suspension consisting of 4.5 g. (0.0294 mole) of 2-methoxynicotinic acid (the product of Preparation A) in 500 ml. of distilled water, there were added 4.7 g. (0.0294 mole) of bromine in one full portion (i.e., all at once) and the resulting mixture was then allowed to stir at room temperature (~20° C.) for a period of approximately 16 hours (i.e., overnight). Upon completion of this step, the pale yellow suspension was then filtered and the recovered solid product was air-dried on the filter funnel to ultimately yield 4.64 g. of crude material in the form of a pale yellow solid. Recrystallization of the latter material from ethyl acetate then gave 3.47 g. (51%) of pure 5-bromo-2-methoxynicotinic acid (m.p. 158°–160° C.) in the form of fluffy white needles. The pure product was further characterized by means of nuclear magnetic resonance data.

PREPARATION J

In a 50 ml. round-bottomed reaction flask equipped with stirring bar and reflux condenser, there were placed 1.0 g. (0.0043 mole) of 5-bromo-2-methoxynicotinic acid (the product of Preparation I) and 10 ml. of methanol, followed by 50 μl. of concentrated sulfuric acid. The resulting reaction mixture was then refluxed for a period of approximate 16 hours (i.e., overnight). Upon completion of this step, the mixture was cooled to room temperature (~20° C.) and filtered, and the recovered precipitate was dried to constant weight to ultimately yield 695.8 mg. (66%) of pure methyl 5-bromo-2-methoxynicotinate (m.p. 90°–101° C.) in the form of a fluffy white solid. The pure product was further characterized by means of nuclear magnetic resonance data.

PREPARATION K

In a dry 25 ml. three-necked, round bottomed reaction flask equipped with nitrogen-inlet tube, rubber septum and glass stopper, there were placed 2.1 g. (0.00795 mole) of methyl 5-bromo-2-methoxynicotinate (the product of Preparation J), 700 μl. (0.00954 mole) of acetone and 15 ml. of dry tetrahydrofuran, followed by 515.3 mg. (0.00954 mole) of dry sodium methoxide which was added all at once while under a dry nitrogen atmosphere, with constant agitation being maintained throughout the course of the entire addition step. The resulting reaction mixture was then stirred at room temperature (~20° C.) for a period of approximately 16 hours (i.e., overnight,), followed by filtration to remove the precipitated product. In this way, there were ultimately obtained, after drying under a high vacuum, 1.72 g. (73.5%) of 3-acetonylcarbonyl-5-bromo-2-methoxypyridine as the sodium salt in the form of an off-white solid.

PREPARATION L

In a 100 ml. three-necked, round-bottomed reaction flask equipped with magnetic stirring bar, reflux condenser, nitrogen-inlet tube, glass stopper and rubber septum, there were placed 1.72 g. (0.00585 mole) of the sodium salt of 3-acetonylcarbonyl-5-methoxypyridine (the product of Preparation K) dissolved in 25 ml. of glacial acetic acid (all under a dry nitrogen atmosphere). The flask and contents was then immersed in an oil bath preheated to 100° C. After a period of five minutes, 2.5 ml. of 48% hydrobromic acid was added via a syringe and the reaction mixture was stirred at 100° C. for a period of 30 minutes. Upon completion of this step, the mixture was cooled quickly to room temperature (~20° C.) by means of an ice-bath and then diluted with 25 ml. of water. The resulting aqueous solution was next extracted with three-20 ml. portions of chloroform, and the combined organic layers were subsequently washed with two-10 ml. portions of 0.5N aqueous sodium hydroxide, one-10 ml. portion of water and one-10 ml. portion of brine. After drying the washed organic layer over anhydrous magnesium sulfate and filtering to remove the drying agent, the product was recovered from the clear filtrate by concentrating same in vacuo to ultimately yield 880 mg. (63%) of pure 6-bromo-2-methyl-4H-pyrano[2,3-b]pyridin-4-one in the form of a yellow solid. The pure product was characterized by means of nuclear magnetic resonance data.

PREPARATION M

In a 35 ml. three-neck, round-bottomed flask equipped with magnetic stirring bar, nitrogen-inlet tube and glass stopper, there were placed 116.1 mg. (0.00305 mole) of lithium aluminum hydride and 3.0 ml. of dry tetrahydrofuran while under a dry nitrogen atmosphere. The resulting suspension was then cooled to −78° C. with stirring, followed by the careful addition of 700 mg. (0.00291 mole) of 6-bromo-2-methyl-4H-pyrano[2,3-b]pyridin-4-one (the product of Preparation L) in 10 ml. of tetrahydrofuran, which was added in a dropwise manner. Upon completion of this step, the resulting reaction mixture was stirred at −78° C. for a period of approximately 16 hours. At this point, 721 μl. of glacial acetic acid was carefully added to the stirred solution and the spent reaction mixture was then further stirred at −78° C. for a period of ten minutes. After adding 10 ml. of saturated aqueous sodium potassium tartrate and 10 ml. of methylene chloride to the cooled mixture, it was allowed to stir at room temperature (~20° C.) for a period of three hours and then filtered to remove a yellow solid. The resulting filtrate was saved and the methylene chloride layer separated therefrom, followed by washing with water (3×10 ml.) and brine (1×10 ml.) and then drying over anhydrous magnesium sulfate. After removal of the drying agent by means of filtration and the solvent by means of evaporation under reduced pressure, there was obtained 467.3 mg. of crude product in the form of a yellow solid. Further purification was then achieved by means of column chromatography, using a flash column of alumina (20 mm.×175 mm.) and 30% ethyl acetate/hexane as the eluant, and collecting 5 ml. samples. In this manner, there was ultimately obtained 185.8 mg. (26%) of pure 6-bromo-2,3-dihydro-2-methyl-4H-pyrano[2,3- b]pyridin-4-one in the form of a pale yellow solid. The pure product was further characterized by means of nuclear magnetic resonance data.

PREPARATION N

In a three-necked, round-bottomed reaction flask equipped with mechanical stirrer and nitrogen-inlet tube, there were placed 17.13 g. (0.085 mole) of methyl 5-chloro-2-methoxynicotinate (the product of Preparation D) in ca. 100 ml. of dry tetrahydrofuran while under a nitrogen atmosphere, followed by the addition thereto of 12.5 ml. (0.1275 mole) of ethyl acetate (1.5 equivalents) and 6.0 g. (0.1105 mole) of sodium methoxide (1.3 equivalents) with constant agitation being maintained throughout the course of the entire addition step. The resulting reaction mixture was then heated to reflux for a period of three hours, followed by the addition thereto of 6 ml. (0.061 mole) of ethyl acetate and 3.0 g. (0.05525 mole) of sodium methoxide. After stirring the final reaction mixture at reflux temperature for a period of six hours and then cooling to room temperature ($\sim 20°$ C.), it was filtered through a 25–50 $\mu$m fritted-glass filter funnel and the isolated solid subsequently dissolved in 100 ml. of water and acidified to pH 1.0. The aqueous layer was next extracted with two-50 ml. portions of diethyl ether, and the combined ethereal extracts were subsequently dried over anhydrous magnesium sulfate and filtered After removal of the drying agent by means of filtration and the solvent by means of evaporation under reduced pressure, there were finally obtained 11.73 g. (57%) of pure 5-chloro-3-methoxycarbonylacetyl-2-methoxypyridine, m.p. 59°–61.5° C. The pure product was further characterized by means of nuclear magnetic resonance data.

PREPARATION O

A mixture consisting of 755 mg. (0.003125 mole) of 5-chloro-3-methoxycarbonylacetyl-2-methoxypyridine (the product of Preparation N) in 10 ml. of 1N aqueous sodium hydroxide solution was refluxed for a period of one hour and then stirred for 16 hours while at room temperature ($\sim 20°$ C.). Upon completion of this step, the stirred reaction mixture was acidified to pH 1.0 with 1N hydrochloric acid and then extracted with three-15 ml. portions of methylene chloride. The combined organic layers were next successively washed with 2% aqueous sodium bicarbonate solution and water, and finally dried over anhydrous magnesium sulfate. After removal of the drying agent by means of filtration and the solvent by means of evaporation under reduced pressure, there was obtained 580 mg. (71%) of pure 3-acetyl-5-chloro-2-methoxypyridine in the form of a residual yellow oil. The pure product was characterized by means of nuclear magnetic resonance data.

PREPARATION P

In a three-necked, round-bottomed reaction flask equipped with mechanical stirrer and nitrogen-inlet tube, there were placed 4.60 g. (0.0248 mole) of 3-acetyl-5-chloro-2-methoxypyridine (the product of Preparation O) in 50 ml. of dry tetrahydrofuran while under a dry nitrogen atmosphere, followed by the addition of three equivalents (6.0 ml.) of ethyl formate and 1.2 equivalents of 50% sodium hydride (1.43 g.), the latter being added in a portionwise manner, with constant agitation being maintained throughout the course of the entire addition step. The resulting mixture was then stirred at room temperature ($\sim 20°$ C.) for a period of approximately 64 hours, followed by filtration through a 25–50 $\mu$m. fritted-glass filter funnel. After washing the filtered product with 20 ml. of ethyl acetate and vacuum drying to constant weight, there were ultimately obtained 5.37 g. (94%) of 3-formylmethylcarbonyl-5-chloro-2-methoxypyridine as the sodium salt in the form of a light yellow powder, m.p. >250° C.

PREPARATION Q

A solution consisting of 5.37 g. (0.233 mole) of the sodium salt of 3-formylmethylcarbonyl-5-chloro-2-methoxypyridine (the product of Preparation P) dissolved in 73 ml. of glacial acetic acid at 100° C. was stirred in a reaction flask and then treated with 7.3 ml. of 48% hydrobromic acid at this same temperature. The resulting reaction mixture was then stirred at 100° C. for a period of 15 minutes and finally cooled to room temperature ($\sim 20°$ C.) with the aid of an ice-bath. Upon completion of this step, the cooled mixture was poured into 100 ml. of water and next extracted with three-50 ml. portions of methylene chloride. The organic extracts were then combined and subsequently washed with 50 ml. of 2% aqueous sodium hydroxide solution and 50 ml. of water, followed by drying over anhydrous magnesium sulfate. After removal of the drying agent by means of filtration and the solvent by means of evaporation under reduced pressure, there were ultimately obtained 1.70 g. (40%) of pure 6-chloro-4H-pyrano[2,3-b]pyridin-4-one as the desired final product. The pure product was characterized by means of nuclear magnetic resonance data.

PREPARATION R

To a stirred solution consisting of 1.0 g. (0.0055 mole) of 6-chloro-4H-pyrano[2,3-b]pyridin-4-one (the product of Preparation Q) dissolved in 18 ml. of tetrahydrofuran and 36 ml. of toluene at $-78°$ C., there were added 6.0 ml. of a 1M solution of diisobutyl—aluminum hydride in toluene. The resulting mixture was then stirred at $-78°$ C. for a period of 2.5 hours. Upon completion of this step, the reaction was quenched by the addition of 0.51 ml. of glacial acetic acid dissolved in 3 ml. of tetrahydrofuran. After allowing the spent reaction mixture to gradually warm to room temperature ($\sim 20°$ C.), it was poured into 100 ml. of water and the resulting aqueous layer was acidified to pH 2.0 by the addition thereto of dilute hydrochloric acid. The two layers were then separated, and the separated aqueous layer was thereafter twice-extracted with 75 ml. of methylene chloride. The combined organic layer were then dried over anhydrous magnesium sulfate and filtered, and the resulting filtrate subsequently evaporated in vacuo to give 715 mg. (71%) of pure 6-chloro-2,3-dihydro-4H-pyrano[2,3-b]pyridin-4-one in the form of a solid product (m.p. 120°–123° C.). The pure product was further characterized by means of nuclear magnetic resonance data.

PREPARATION S

The procedure described in Preparation D to prepare methyl 5-chloro-2-methoxynicotinate is repeated here except that 2-methoxynicotinic acid (see D. E. Kuhla et al. in U.S. Pat. No. 3,879,403) is the starting material employed in place of 5-chloro-2-methoxynicotinic acid, using the same molar proportions as before. In this particular case, the corresponding final product obtained is methyl 2-methoxynicotinate [identical with the compound described by Kitagawa et al., in Chem. Pharm. Bull., Vol. 26, p. 1403 (1978)].

PREPARATION T

A stirred solution consisting of 8.6 g. (0.050 mole) of methyl 2-methoxynicotinate (the product of Preparation S) dissolved in 25 ml. of trifluoroacetic anhydride was treated with 6.0 g. (0.075 mole) of ammonium nitrate, which was added in a portionwise manner. Upon completion of this step, the resulting mixture was stirred at room temperature ~20° C.) for a period of two hours and then poured into 30 ml. of an ice/water mixture. The yellow crystals which formed at this point were subsequently collected by means of suction filtration and then dissolved in chloroform. The water layer was next separated therefrom, and the resulting organic solution was subsequently dried over anhydrous magnesium sulfate. After removal of the drying agent by means of filtration and the solvent by means of evaporation under reduced pressure, there were obtained 6.5 g. (60%) of pure methyl 5-nitro-2-methoxynicotinic acid (m.p. 98°–99.5°.C.) as the residual material. The pure product was characterized by means of nuclear magnetic resonance data.

PREPARATION U

A mixture consisting of 1.08 g. (0.005 mole of methyl 5-nitro-2-methoxynicotinate (the product of Preparation T) and 5.64 g. (0.0025 mole) of stannous chloride dihydrate in 10 ml. of ethyl acetate was refluxed for a period of 20 minutes. Upon completion of this step, the resulting reaction mixture was poured into 50 ml. of ice water and treated with sodium bicarbonate to adjust the pH of the solution to pH 7.0. The resulting aqueous solution was then extracted with three-50 ml. portions of ethyl acetate, and the combined organic extracts were subsequently washed with one-50 ml. portion of water and then dried over anhydrous magnesium sulfate. After removal of the drying agent by means of filtration and the solvent by means of evaporation under reduced pressure, there were obtained 800 mg. (86%) of pure methyl 5-amino-2-methoxynicotinate (m.p. 109°–110.5° C.) as the residual material. The pure product was characterized by means of nuclear magnetic resonance data.

PREPARATION V

A stirred solution consisting of 1.5 g. (0.00806 mole) of methyl 5-amino-2-methoxynicotinate (the product of Preparation U) dissolved in 25 ml. of ethanol was treated with 12 ml. of 23% hydrofluorosilic acid. The resulting reaction mixture was then cooled in ice, and the white salt product which formed was subsequently collected by means of suction filtration. The salt product was then suspended in 25 ml. of glacial acetic acid and sufficient butyl nitrite was added to the suspension in a dropwise manner in order to effect complete dissolution of the salt. The resulting solution was then diluted with 40 ml. of diethyl ether and cooled to 0° C. The desired diazonium salt, which separated at this point as an oil, was then collected and subsequently suspended in 20 ml. of ethanol to form a new white solid salt. The latter solid material was then collected by means of suction filtration (under a nitrogen blanket), washed with three-10 ml. portions of diethyl ether and dried under a high vacuum to afford 550 mg. (20%) of 3-carbomethoxy-2-methoxypyridine-5-diazonium hydrohexafluorosilicate, m.p. 124°–127° C. (decomp.).

The above diazonium salt (550 mg., 0.0016 mole) was then suspended in 10 ml. of xylene and heated to an oil bath temperature of 130° C., at which point nitrogen evolution commenced and the reaction mixture became oily in appearance. The bath temperature was then raised to 140° C. and heating of the mixture was continued at this point for a period of 15 minutes. Upon completion of this step, the reaction mixture was allowed to cool to room temperature (~20° C.) and then filtered through a glass wool plug. Concentration of the resulting filtrate to near dryness while under reduced pressure then gave 293 mg. of the desired 5-fluoro compound. Further purification of the product was then achieved via radial chromatography on silica gel, using 15% ethyl acetate/hexane as the eluant, to ultimately afford 210 mg. (68%) of pure methyl 5-fluoro-2-methoxynicotinate. The overall yield of pure product, based on the methyl 5-amino-2-methoxynicotinate starting material, amounted to 14% of the theoretical value. The pure product was characterized by means of nuclear magnetic resonance data.

PREPARATION W

A stirred solution consisting of 2.0 g. (0.0106 mole) of methyl 5-fluoro-2-methoxynicotinate (the product of Preparation V) dissolved in 20 ml. of dry tetrahydrofuran was treated with 0.91 ml. of acetone (1.3 equivalents) and 670 mg. of dry sodium methoxide (1.3 equivalents), which was added all at once while under a dry nitrogen atmosphere. Stirring was then continued at room temperature (~20° C.) for a period of approximately 16 hours, followed by concentration of the mixture under reduced pressure to give a thick oil. The latter material was then diluted with 20 ml. of 1N hydrochloric acid, and the resulting acidified aqueous solution was thereafter extracted with three-20 ml. portions of diethyl ether. The ethereal extracts were next combined and subsequently dried over anhydrous magnesium sulfate. After removal of the drying agent by means of filtration and the solvent by means of evaporation under reduced pressure, there were ultimately obtained 1.94 g. (87%) of 3-acetonylcarbonyl-5-fluoro-2-methoxypyridine in the form of a brown oil. The product was characterized by means of nuclear magnetic resonance data.

PREPARATION X

A solution consisting of 1.94 g. (0.00928 mole) of 3-acetonylcarbonyl-5-fluoro-2-methoxypyridine (the product of Preparation W) dissolved in 30 ml. of glacial acetic acid at 100° C. was treated with 3.0 ml. of 48% hydrobromic acid and stirred at this point for a period of 20 minutes. Upon completion of this step, the reaction mixture was cooled to room temperature (~20° C.) and poured into 100 ml. of water. The resulting aqueous solution was next extracted with three-30 ml. portions of methylene chloride, and the combined organic layers were subsequently washed with one-50 ml. portion of water and one-50 ml. portion of 2% aqueous sodium hydroxide solution. After drying the washed organic layer over anhydrous magnesium sulfate and filtering to remove the drying agent, the resulting clear filtrate was subsequently concentrated in vacuo to afford 645 mg. of 6-fluoro-2-methyl-4H-pyrano[2,3-b]pyridin-4-one. Radial chromatography of the latter material on silica gel, using 1% methanol/chloroform as the eluant, then gave 440 mg. (26%) of pure 6-fluoro-2-methyl-4H-pyrano[2,3-b]pyridin-4-one.

The pure product was characterized by means of nuclear magnetic resonance data.

PREPARATION Y

To a stirred solution consisting of 440 mg. (0.00246 mole) of 6-fluoro-2-methyl-4-pyrano[2,3-b]-pyridin-4-one (the product of Preparation X) dissolved in 5.0 ml. of tetrahydrofuran and 10 ml. of toluene at −78° C., there were added 3.0 ml. of a 1M solution of diisobutylaluminum hydride in toluene. The resulting mixture was then stirred at −78° C. for a period of 2.5 hours. Upon completion of this step, the reaction was quenched by the addition of 0.25 ml. of glacial acetic acid. After allowing the spent reaction mixture to gradually warm to room temperature (~20° C.), it was poured into 20 ml. of water and the resulting aqueous layer acidified to pH 3.0 by the addition thereto of dilute hydrochloric acid. The two layers were then separated, and the separated aqueous layer was thereafter extracted with three-20 ml. portions of diethyl ether. The combined organic layers were then dried over anhydrous magnesium sulfate and filtered, and the resulting filtrate subsequently concentrated in vacuo to ultimately afford 110 mg. (25%) of pure 6-fluoro-2,3-dihydro-4H-pyrano[2,3-b]pyridin-4-one in the form of a residual oil. The pure product was further characterized by means of nuclear magnetic resonance data.

EXAMPLE 1

A stirred mixture consisting of 2.3 g. (0.0116 mole) of 6-chloro-2,3-dihydro-2-methyl-4H-pyrano[2,3-b]pyridin-4-one (the product of Preparation G), 1.5 g. (0.0232 mole) of potassium cyanide, 6.6 g. (0.0696 mole) of ammonium carbonate and 1.2 g. (0.0116 mole) of sodium bisulfite in 100 ml. of 50% aqueous methanol was heated in a wired-down stoppered flask at 80°–90° C. for a period of approximately 16 hours (i.e., overnight). Upon completion of this step, the reaction mixture was poured into a water/ethyl acetate mixture and acidified with 6N hydrochloric acid. After extracting the resulting aqueous organic solution with ethyl acetate, there were obtained several organic extracts that were later combined, washed with saturated brine and subsequently dried over anhydrous magnesium sulfate. Upon removal of drying agent by means of filtration and the solvent by means of evaporation under reduced pressure, there was ultimately obtained a yellow oil as the residual material. Crystallization of the latter material twice from chloroform containing a little methanol then gave 13 mg. of pure (±)-cis-6'-chloro-2',3'- dihydro-2'-methyl-spiro-[imidazolidine-4,4'-4'H-pyrano[2,3-b]pyridine]-2,5-dione, m.p. >250° C. The pure product was further characterized by means of mass spectroscopy and thin layer chromatography, in addition elemental analysis.

Anal. Calcd. for $C_{11}H_{10}ClN_3O_3$: C, 49.36; H, 3.76; N, 15.70. Found: C, 49.15; H, 3.78; 15.49.

EXAMPLE 2

A stirred mixture consisting of 500 mg. (0.0025 mole) of 6-chloro-2,3-dihydro-2-methyl-4H-pyrano[2,3-b]pyridin-4-one (the product of Preparation G), 325 mg. (0.0050 mole) of potassium cyanide, 1.7 g. (0.0175 mole) of ammonium carbonate and 2.5 g. (0.042 mole) of acetamide was heated in a wired-down stoppered flask at 80° C. for a period of approximately 16 hours (i.e., overnight). Upon completion of this step, the reaction mixture was cooled to room temperature (~20° C.) to afford a solid mass which was thereafter partitioned between ethyl acetate and water, followed by acidification with 6N hydrochloric acid. The acidified aqueous organic solution was then treated with activated carbon and filtered, followed by extraction of the resulting clear aqueous filtrate with ethyl acetate. The combined organic extracts were next washed with saturated brine and finally dried over anhydrous magnesium sulfate. After removal of the drying agent by means of filtration and the solvent by means of evaporation under reduced pressure, there was obtained a dark brown oil as the residual liquid. Crystallization of the latter material from chloroform/methanol (95:5 by volume) then gave 20 mg. (3%) of pure (±)-cis-6'-chloro-2',3'-dihydro-2'-methyl-spiro-[imidazolidine-4,4'-4'H-pyrano[2,3-b]pyridine]-2,5-dione, m.p. >250° C. This product was identical in very respect with the product of Example 1, as particularly attested to by thin layer chromatography studies. The pure product was further characterized by means of nuclear magnetic resonance data.

EXAMPLE 3

A mixture consisting of 5.0 g. (0.025 mole) of 6-chloro-2,3-dihydro-2-methyl-4H-pyrano[2,3-b]pyridin-4-one (the product of Preparation G), 3.25 g. (0.050 mole) of potassium cyanide, 16.8 g. (0.175 mole) of ammonium carbonate and 2.6 g. (0.025 mole) of sodium bisulfite in 50 ml. of formamide was placed in a stainless-steel autoclave and heated at 40° C. for a period of four days. Upon completion of this step, the reaction mixture was cooled to room temperature (~20° C.), poured into water and then acidified to pH 3.0 with 6N hydrochloric acid. The precipitated product so obtained was subsequently collected by means of suction filtration and air-dried to constant weight to afford 3.3 g. of crude material. Recrystallization of the latter material from 125 ml. of chloroform/methanol (9:1 by volume) then gave 2.26 g. (34%) of pure (±)+-cis-6'-chloro-2',3'-dihydro-2'-methyl-spiro-[imidazolidine-4,4'-4'H-pyrano[2,3-b]pyridine]-2,5-dione, m.p. >250° C. A second crop of crystals consisting of 600 mg. (9%) of the same pure product was obtained from the mother liquor. The total yield of pure product was 43% of the theoretical value. This product was identical in every respect with the product of Example 1 and was further characterized by means of nuclear magnetic resonance data (also identical with the product of Example 2).

EXAMPLE 4

A. A mixture consisting of 39.3 g. (0.20 mole) of 6-chloro-2,3-dihydro-2-methyl-4H-pyrano[2,3-b]-pyridin-4-one (the product of Preparation H) 26 g. (0.40 mole) of potassium cyanide, 134.4 g. (0.40 mole of ammonium carbonate and 25 g. (0.24 mole) of sodium bisulfite in 400 ml. of formamide was placed in a stainless-steel autoclave and heated at 50° C. for a period of three days. Upon completion of this step, the reaction mixture was cooled to room temperature (~20° C.), diluted with water (up to 3500 ml.) and filtered to remove a small amount of insoluble material. The resulting filtrate was then acidified to pH 2.5 with concentrated hydrochloric acid and allowed to stir at room temperature for a period of 30 minutes. The precipitated product so obtained was subsequently collected by means of suction filtration and air-dried to constant weight to afford 33 g. of crude material. Recrystallization of the latter material from 1200 ml. of 9:1 (by volume) chloroform/methanol (which was accomplished by first reducing the total volume to 600 ml. and then allowing the resulting solution to stir at room temperature for ca. 16 hours) then gave 15.4 g. (29%) of pure (±)-cis-6'-chloro-2',3'-dihydro2'-methyl-spiro-[imidazolidine-4,4'-4'H-pyrano[2,3-b]-pyridine]-2,5-dione (m.p. >250° C.), which was identical in every respect with the product of the previous examples (as particularly attested to by nuclear magnetic resonance data). A second and third crystalline crop consisting respectively of 9.1 g. (17%) and 2.1 g (4%) of the same pure product were later obtained from the mother liquor. The total yield of pure product (2'-CH3, 4'-NH cis; 2'R,4'S/2'S,4'R) was 50% (26.6 g.) of the theoretical value.

B. The mother liquor also contained a small amount of the trans-isomer which was isolated by preparative high pressure liquid chromatography (HPLC) using multiple injections on a Zorboy Silica Prep column, 21.2×25 cm., and eluting with 5% methanol in chloroform. Collection of the more polar fractions gave 40 mg. of crude trans-isomer. Recrystallization of the latter material from ethyl acetate/hexane then yielded 26.5 mg. of pure (+)-trans-6'-chloro-2',3'-dihydro-2'-methyl-spiro-[imidazolidine-4,4'-4'H-pyrano[2,3-b]pyridine]-2,5-dione (m.p. >250° C.). The pure product (2'-CH3, 4'—NH trans; 2'S,4'S/2'R,4'R) was characterized by means of nuclear magnetic resonance data.

EXAMPLE 5

A stirred mixture consisting of 100 mg. (0.00037 mole) of (±)-cis-6'-chloro-2',3'-dihydro-2'-methyl-spiro-[imidazolidine-4,4'-4'H-pyrano[2,3-b]pyridine]-2,5-dione (the product of Example 4A), 3.0 ml. of glacial acetic acid and 1.0 ml. of 30% hydrogen peroxide was heated at 85° C. for a period of approximately 16 hours (i.e., overnight). Upon completion of this step, the reaction mixture was cooled to room temperature (~20° C.), diluted with water and filtered to remove the resulting precipitate therefrom. After air-drying the recovered product to constant weight, there was obtained 30 mg. (28%) of pure (+)-6-chloro-2',3'- dihydro-2'-methyl-spiro-[imidazolidine-4,4'-4'H-pyrano[2,3-b]pyridine]-2,5-dione-8'-oxide, m.p. >250° C. The pure product was further characterized by means of mass spectroscopy and thin layer chromatography, in addition to elemental analysis.

Anal. Calcd. for $C_{11}H_{10}ClN_3O_4$: C, 46.58; H, 3.55; N, 14.81. Found: C, 46.42; H, 3.56; N, 14.67.

EXAMPLE 6

A mixture consisting of 360.6 mg. (0.00149 mole) of 6-bromo-2,3-dihydro-2-methyl-4H-pyrano[2,3-b]-pyridin-4-one (the product of Preparation M), 194.1 mg. (0.00298 mole) of potassium cyanide, 1.0 g. (0.0105 mole) of ammonium carbonate and 154.8 mg. (0.00149 mole) of sodium bisulfite in 10 ml. of formamide was placed in a 100 ml. wired-down stoppered, round-bottomed flask equipped with magnetic stirring bar and heated with stirring at 40°–45° C. for a period of approximately 16 hours (i.e., overnight). Upon completion of this step, the amber-colored solution was allowed to cool to room temperature (~20° C.) and then diluted with 10 ml. of water (the pH of the solution was now about pH 9–10). The pH was then adjusted to pH 2–3 by the addition of 6N hydrochloric acid in a dropwise manner, and the resulting solution was stirred at room temperature for a period of 1.5 hours. The precipitated product so obtained (as a white solid) was subsequently collected by means of suction filtration and air-dried to constant weight to afford 176.7 mg. of crude material. Recrystallization of the latter material from isopropyl alcohol/isopropyl ether then gave 115.5 mg. (25%) of pure (±)-cis-6'-bromo-2',3'-dihydro-2'-methyl-spiro-[imidazolidine-4,4'-4'H-pyrano[2,3-b]pyridine]-2,5-dione, m.p. >250° C. The pure product was further characterized by means of mass spectroscopy and nuclear magnetic resonance data, in addition to elemental analysis.

Anal Calcd. for $C_{11}H_{10}BrN_3O_3$: C, 42.32; H, 3.23; N, 13.45. Found: C, 41.95; H, 3.25; N, 13.18.

EXAMPLE 7

A mixture consisting of 715 mg. (0.00389 mole) of 6-chloro-2,3-dihydro-4H-pyrano[2,3-b]pyridin-4-one (the product of Preparation R), 500 mg. (0.00128 mole) of potassium cyanide, 2.58 g. (0.027 mole) of ammonium carbonate and 400 mg. (0.00386 mole) of sodium bisulfite in 7.0 ml. of formamide was placed in a 65 ml. wired-down stoppered, round-bottomed flask and heated with stirring at 52° C. for a period of 15 hours. Upon completion of this step, the reaction mixture was cooled to room temperature (>20° C.) and diluted with 30 ml. of water. The resulting aqueous solution was then acidified to pH 3.0 with concentrated hydrochloric acid, and the precipitated product so obtained was subsequently collected by means of suction filtration. After washing with water on the filter funnel and drying under a high vacuum to constant weight, there was ultimately obtained 848 mg. (84%) of crude product. Recrystallization of the latter material from 60 ml. of chloroform/methanol (9:1 by volume) then gave 752 mg. (52%) of pure (+)-6-chloro-2',3'-dihydro-spiro-[imidazolidine-4,4'-4'H-pyrano[2,3-b]pyridine]-2,5-dione as a chloroform solvate, m.p. 265°–266° C.

Anal. Calcd. for $C_{10}H_8ClN_3O_3CHCl_3$: C, 35.42; H, 2.43; N, 11.26. Found: C, 35.84; H, 2.51; N, 11.55.

EXAMPLE 8

A suspension consisting of 500 mg. (0.0018 mole) of (+)-cis-6'-chloro-2',3'-dihydro-2'-methyl-spiro-[imidazolidine-4,4'-4'H-pyrano[2,3-b]pyridine]-2,5-dione (the product of Example 4A) and 50 mg. of 10% palladium-on-carbon catalyst in 10 ml. of methanol containing 377 mg. (0.0036 mole) of triethylamine (0.5 ml.) was prepared by combining said ingredients together in a reaction flask while under a nitrogen atmosphere. The resulting mixture was then hydrogenated at room temperature (~20° C.), while under atmospheric pressure, for a period of approximately 16 hours (i.e., overnight). At this point, no further uptake of hydrogen gas could be detected. The reaction solution containing the final product was then recovered from the flask by means of decantation and filtered through Super-Cel (siliceous earth) to remove the catalyst, followed by washing of the filtered material with a small amount of methanol. The combined filtrate and washings were then saved, and subsequently concentrated in vacuo to yield a white foam. Trituration of the latter material with chloroform then gave a white solid product, which was subsequently collected by means of suction filtration and air-dried to constant weight to ultimately afford 450 mg. (86%) of pure (±)-cis-2',3'-dihydro-2-methyl-spiro-[imidazolidine-4,-4'-4'H-pyrano[2,3-b]pyridine]-2,5-dione, m.p. 150° C. (decomp.). The pure product was further characterized by means of mass spectroscopy, thin layer chromatography and nuclear magnetic resonance data, in addition to elemental analysis.

Anal. Calcd. for $C_{11}H_{11}N_3O_3 \cdot 0.4CHCl_3$: C, 48.73; H, 4.09; N, 14.95. Found: C, 49.01; H, 4.12; N, 15.10.

EXAMPLE 9

A mixture consisting of 110 mg. (0.0061 mole) of 6-fluoro-2,3-dihydro-2-methyl-4H-pyrano[2,3-b]pyridin-4-one (the product of Preparation Y) 78 mg. (0.00075 mole) of potassium cyanide, 400 mg. (0.00512 mole) of powdered ammonium carbonate and 62 mg. (0.00061 mole) of sodium bisulfite in 1.0 ml. of formamide was placed in a 6 ml. wired-down stoppered, round-bottomed flask and heated with stirring at 51° C. for a period of 24 hours. Upon completion of this step, the reaction mixture was cooled to room temperature (~20° C.) and allowed to stir at that point for a period of five days prior to being diluted with 10 ml. of water. The resulting aqueous solution was then acidified to pH 3.0 with dilute hydrochloric acid and next extracted with three-10 ml. portions of ethyl acetate. The combined organic layers were then dried over anhydrous magnesium sulfate and filtered, and the resulting filtrate subsequently concentrated in vacuo to afford to a residual oil that was thereafter triturated with 3.0 ml. of hot chloroform/methanol (9:1 by volume). After cooling to room temperature, there was eventually obtained 42 mg. of a yellow crystalline powder. Recrystallization of the latter material from ca. 7.0 ml. of chloroform/methanol (9:1 by volume) then gave 28 mg. (16%) of pure (+)-cis-6'-fluoro-2',3'-di-hydro-2'-methyl-spiro-[imidazolidine-4,4'-4H-pyrano-[2,3-b]pyridine]-2,5-dione (as a one third chloroform solvate) in the form of white powdery flakes melting at 231°-232.5° C. The pure product was further characterized by means of mass spectroscopy, nuclear magnetic resonance data and infrared absorption spectra, in addition to elemental analysis.

Anal. Calcd. for $C_{11}H_{10}FN_3O_3 \cdot 0.33CHCl_3$: C, 46.78; H, 3.58; N, 14.43. Found: C, 46.98; H, 3.80; N, 14.33

EXAMPLE 10

A. The cis-isomer of (+)-6'-chloro-2',3'-dihydro-2'-methyl-spiro-[imidazolidine-4,4'-4H-pyrano[2,-3-b]pyridine]-2,5-dione (965 mg., 0.0036 mole) was added to a solution of 1.18 g. (0.0036 mole) of cinchonine methohydroxide in 24 ml. of water [prepared according to the method of R. T. Major et al., as described in the *Journal of the American Chemical Society*, Vol. 63, p. 1368 (1941)]. The resulting mixture was then evaporated in vacuo, followed by crystallization of the residue from isopropanol-isopropyl ether to give 919 mg. of a white solid, which was subsequently collected by means of suction filtration while the mother liquor was saved. The solid material so obtained was then recrystallized from isopropanol to yield 680 mg. (65%) of the enantiomerically pure (4'S)(2'R)-salt. A 400 mg. sample of this salt was next treated with 17 ml. of 1N hydrochloric acid, and the resulting solution extracted with three-10 ml. portions of ethyl acetate. The ethyl acetate extracts were thereafter combined, dried and evaporated to ultimately yield 172 mg. of a white solid material, which was later recrystallized from ethyl acetate/hexane to afford 129 mg. (70%) of pure (4'S)(2'R)-6'-chloro-2',3'-dihydro-2'-methyl-spiro-[imidazolidine-4,4'-4'H-pyrano[2,3-b]pyridine]-2,5-dione, m.p. >250° C.; $[\alpha]_D^{20°} +235.7°$ (c=1, methanol).

Anal. Calcd. for $C_{11}H_{10}ClN_3O_3$: C, 49.36; H, 3.76; N, 15.70. Found: C, 49.00; H, 3.85; N, 15.34.

B. The saved original mother liquor, obtained from above, was next concentrated in vacuo to give 990 mg. of a white solid. A 890 mg. sample of the latter material was then treated with 10 ml. of 1N hydrochloric acid, and the resulting solution extracted with three-15 ml. portions of ethyl acetate. The ethyl acetate extracts were thereafter combined, dried and evaporated in vacuo to near dryness to ultimately afford a residue which on treatment with ethyl acetate/hexane deposited 120 mg. of a racemic crop. Concentration of the mother liquor, followed by crystallization of the residue from ethyl acetate/hexane then gave 142.6 mg. of pure (2'S)(4'R)-6'-chloro-2',3'-dihydro-2'-methyl-spiro-[imidazolidine-4,4'-4'H-pyrano[2,3-b]pyridine]-2,5-dione, m.p. >250° C.; $[\alpha]_D^{20°} -226.3°$ (c=1, methanol).

Anal. Calcd. for $C_{11}H_{10}ClN_3O_3$: C, 49.36; H, 3.76; N, 15.70. Found: C, 49.15; H, 3.84; N, 15.37.

EXAMPLE 11

The cis-isomer of (+)-6'-chloro-2',3'-dihydro-2'-methyl-spiro-[imidazolidine-4,4'-4'H-pyrano[2,3-b]pyridine]-2,5-dione (2.67 g., 0.01 mole) was heated under reflux with 15.8 g. (0.05 mole) of barium hydroxide octahydrate in 100 ml. of water for a period of four days. After cooling to room temperature (~20° C.), the aqueous mixture was diluted with water and then treated dropwise with a solution of 4.8 g. (0.05 mole) of ammonium carbonate. The precipitated solids which formed at this point were then removed by means of filtration, washed with water and the resulting filtrate thereafter concentrated in vacuo to afford a residue. Crystallization of the latter material from methanol then gave as a first crop 1.4 g. (58%) pure cis-4-amino-6-chloro-2,3-dihydro-2-methyl- 4H-pyrano[2,3-b]pyridine-4-carboxylic acid, m.p. 200°-203° C.; mass spectrum, m/e 242.

Anal. Calcd. for $C_{10}H_{11}ClN_2O_3 \cdot 0.75H_2O$: C, 46.87; H, 4.92; N, 10.94. Found: C, 46.89; H, 4.62; N, 10.89.

EXAMPLE 12

A solution consisting of 1.0 g. (0.004 mole) of cis-4-amino-6-chloro-2,3-dihydro-2-methyl-4H-pyrano-[2,3-b]pyridine-4-carboxylic acid (the product of Example 11) dissolved in 220 ml. of water was adjusted to pH 5.0 with 1N hydrochloric acid and treated portion-wise with 640 mg. (0.008 mole) of potassium cyanate, while continuously maintaining the pH of the solution at pH 5.0 with 1N hydrochloric acid for one hour. After stirring the resulting mixture overnight for a period of approximately 16 hours, the pH (which had increased to a value of pH 8.0) was adjusted to pH 3.0 by the addition of 1N hydrochloric acid. The precipitated solids which formed at this point were then collected, washed with water and air-dried to constant weight to give 570 mg. (50%) of pure cis-6-chloro-2,3-dihydro-2-methyl-4-ureido-4H-pyrano[2,3-b]pyridine-4-carboxylic acid, m.p. 209°-210° C.; mass spectrum, m/e 285.

Anal. Calcd. for $C_{11}H_{12}ClN_3O \cdot 0.5H_2O$: C, 44.83; H, 4.44; N, 14.26. Found: C, 44.54; H, 4.13; N, 14.23.

EXAMPLE 13

A slurry consisting of 2.5 g. (0.00875 mole) of cis-6-chloro-2,3-dihydro-2-methyl-4-ureido-4H-pyrano-[2,3-b]pyridine-4-carboxylic acid (the product of Example 12) in 25 ml. of methanol was treated with 1.85 g.

(0.00875 mole) of S-(−)-N-benzyl-α-methyl-benzylamine, and the resultant solution was allowed to evaporate slowly at room temperature (∼20° C.) until crystals formed. The latter crystals were then collected by means of suction filtration and washed with methanol to afford 2.1 g. (97%) of crude (4S)(2R)-hydantoic acid salt, m.p. 168°-170° C. (decomp.). The mother liquor (A) was saved. Recrystallization of the solids (m.p. 168°-170° C.) from methanol then gave as a first crop 1.0 g. (46%) of the pure S-(−)-N-benzyl-α-methylbenzylamine salt of (4S)(2R)-6-chloro-2,3-dihydro-2-methyl-4-ureido-4H-pyrano[2,3-b]pyridine-4-carboxylic acid, m.p. 175°-177° C. (decomp.); $[\alpha]_D^{20°} +58.7°$ (c=1, methanol).

Anal. Calcd. for $C_{11}H_{12}ClN_3O_4 \cdot C_{15}H_{17}N \cdot 0.25H_2O$: C, 62.27; H, 5.93; N, 11.17. Found: C, 62.33; H, 5.87; N, 11.17.

A 500 mg. (0.001 mole) sample of the above pure salt was then dissolved in 5.0 ml. of glacial acetic acid and heated at 90° C for a period of four hours. After cooling to room temperature (∼20° C.), the mixture was diluted with water and extracted with ethyl acetate. The ethyl acetate extract was next dried and evaporated in vacuo to ultimately yield 260 mg. (97%) of pure (4'S)(2'R)-6'-chloro-2',3'-dihydro-2'-methyl-spiro-[imidazolidine-4,4'-4'H-pyrano[2,3-b]-pyridine-2,5-dione, $[\alpha]_D^{20°} +205.4°$ (c=1, methanol).

The saved mother liquor (A), originally obtained in the first step, was next allowed to stand at room temperature for a period of three days and thereafter deposited 87 mg. of the pure (S)(−)-N-benzyl-α-methylbenzylamine salt of (4R)(2S)-6-chloro-2,3-dihydro-2-methyl-4-ureido-4H-pyrano[2,3-b]pyridine-4-carboxylic acid, m.p. 164°-165° C.; −67.6° (c=1, methanol). X-ray analysis confirme the 4R, 2S configuration of this compound.

Anal. Calcd. for $C_{11}H_{12}ClN_3O_4 \cdot C_{15}H_{17}N \cdot CH_3OH$: C, 61.30; H, 6.29; N, 10.59. Found: C, 61.04; H, 6.24; N, 10.57.

EXAMPLE 14

A stirred mixture consisting of 100 mg. (0.00037 mole) of (4'S)(2'R)-6'-chloro-2',3'-dihydro-2'-methyl-spiro-[imidazolidine-4,4'-4'H-pyrano[2,3-b]pyridine]-2,5-dione [the (4'S)(2'R)- product of Example 10A], 3.0 ml. of glacial acetic acid and 1.0 ml. of 30% hydrogen peroxide was heated at 80°-90° C. for a period of approximately 16 hours (i.e., overnight). Upon completion of this step, the reaction mixture was cooled to room temperature (∼20° C.) and diluted with water. The precipitated product was recovered by means of filtration, washed well with water and air-dried to constant weight, followed by further drying in vacuo 15 overnight. In this manner, there was obtained 40 mg. (40%) of pure (4'S)(2'R)-6'-chloro-2',3'-dihydro-2'-methyl-spiro-[imidazolidine-4,4'-4'H-pyrano[2,3-b]pyridine]-2,5-dione-8'-oxide, m.p. >250° C. The pure product was further characterized by means of mass spectroscopy and thin layer chromatography, in additional to elemental analysis.

Anal. Calcd. for $C_{11}H_{10}ClN_3O_4$: C, 46.58; H, 3.55; N, 14.81. Found: C, 46 37; H, 3.52; N, 14.71.

EXAMPLE 15

The following spiro-3-heteroazolone compounds of Examples 4A, 4B, 6-9, 10A, 10B and 14, respectively, were tested for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In every case, the substrate employed was partially purified aldose reductase enzyme obtained from human placenta. The results obtained with each compound are expressed below in terms of their percent inhibition of enzyme activity (%) with respect to the particular concentration level chosen ($10^{-5}$M):

| Compound | % Inhibition at $10^{-5}$M |
| --- | --- |
| Product of Example 4A | 83 |
| Product of Example 4B | 77 |
| Product of Example 6 | 80 |
| Product of Example 7 | 60 |
| Product of Example 8 | 57 |
| Product of Example 9 | 77 |
| Product of Example 10A | 100 |
| Product of Example 10B | 100 |
| Product of Example 14 | 79 |

EXAMPLE 16

The following spiro-3-heteroazolone compounds of Examples 4A, 4B, 6 and 10A, respectively, were tested for their ability to reduce or inhibit sorbitol accumulation in the sciatic nerve and lens of streptozotocinized (i.e., diabetic) rats by the procedure essentially described in U.S. Pat. No. 3,821,383. In the present study, the amount of sorbitol accumulation in the sciatic nerve and lens of each test animal was measured 27 hours after induction of diabetes. The compounds were then administered orally at the dose levels indicated at 4, 8 and 24 hours following the administration of streptozotocin. The results obtained in this manner are presented below in terms of percent inhibition (%) afforded by the test compound as compared to the case where no compound was administered (i.e., the untreated animal where sorbitol levels normally rise from approximately 50-100 mM/g. tissue to as high as 400 mM/g. tissue in the 27-hour test period):

| Compound | Dosage (mg./kg.) | Percent Inhibition (%) | |
| --- | --- | --- | --- |
| | | Sciatic Nerve | Lens |
| Prod. of Ex. 4A | 5.0 | 98 | 89 |
| Prod. of Ex. 4A | 0.25 | 34 | 22 |
| Prod. of Ex. 4B | 0.25 | 13 | 32 |
| Prod. of Ex. 6 | 1.0 | 73 | 67 |
| Prod. of Ex. 10A | 1.0 | 78 | 73 |
| Prod. of Ex. 10A | 0.1 | 43 | 33 |

We claim:

1. A spiro-azolone compound of the formula:

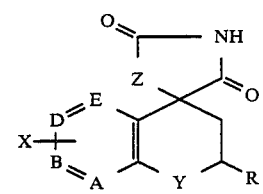

or a base salt thereof with a pharmacologically acceptable cation, wherein

X is hydrogen, fluorine, chlorine, bromine, nitro, trifluoromethyl, $C_1$-$C_4$ alkyl, $C_1$-$C_4$ alkoxy or $C_1$-$C_4$ alkylthio;

Z is methylene, oxygen, sulfur or imino;

Y is oxygen or sulfur; and

R is hydrogen or $C_1$-$C_4$ alkyl; and

—A=B—D=E— represents —N=CH—CH=CH—, —CH=N—CH=CH—, —CH=CH—N=CH— or —CH=CH—CH=N—, or an N-oxide derivative thereof.

2. A compound as claimed in claim 1 wherein Z is methylene.

3. A compound as claimed in claim 1 wherein Z is oxygen.

4. A compound as claimed in claim 1 wherein Z is sulfur.

5. A compound as claimed in claim 1 wherein Z is imino.

6. A compound as claimed in claim 5 wherein —A=B—D=E— is —N=CH—CH=CH—.

7. A compound as claimed in claim 5 wherein —A=B—D=E— is —CH=N—CH=CH—.

8. A compound as claimed in claim 5 wherein —A=B—D=E— is —CH=CH—N=CH—.

9. A compound as claimed in claim 5 wherein —A=B—D=E— is —CH=CH—CH=N—.

10. A compound as claimed in claim 5 wherein —A=B—D=E— is the N-oxide derivative of —N=CH—CH=CH—.

11. A compound as claimed in claim 6 wherein Y is sulfur.

12. A compound as claimed in claim 6 wherein Y is oxygen.

13. A compound as claimed in claim 12 wherein X is hydrogen and R is $C_1$-$C_4$ alkyl.

14. A compound as claimed in claim 13 wherein R is methyl.

15. A compound as claimed in claim 12 wherein X is fluorine and R is $C_1$-$C_4$ alkyl.

16. A compound as claimed in claim 15 wherein X is fluorine at the 6'-position of the molecule and R is methyl.

17. A compound as claimed in claim 12 wherein X is chlorine and R is hydrogen.

18. A compound as claimed in claim 17 wherein X is chlorine at the 6'-position of the molecule 19. A compound as claimed in claim 12 wherein X is chlorine and R is $C_1$-$C_4$ alkyl.

20. A compound as claimed in claim 19 wherein X is chlorine at the 6'-position of the molecule and R is methyl.

21. A compound as claimed in claim 12 wherein X is bromine and R is $C_1$-$C_4$ alkyl.

22. A compound as claimed in claim 21 wherein X is bromine at the 6'-position of the molecule and R is methyl.

23. A compound as claimed in claim 10 wherein Y is oxygen.

24. A compound as claimed in claim 23 wherein X is chlorine and R is $C_1$-$C_4$ alkyl.

25. A compound as claimed in claim 24 wherein X is chlorine at the 6-position of the molecule and R is methyl.

26. (+)-Cis-6'-chloro-2',3'-dihydro-2'-methyl-spiro-[imidazolidine-4,4'-4'H-pyrano[2,3-b]pyridine]-2,5-dione.

27. (4'S)(2'R)-6'-Chloro-2',3'-dihydro-2'-methyl-spiro-[imidazolidine-4,4'-4'H-pyrano[2,3-b]pyridine]-2,5-dione.

28. A pharmaceutical composition suitable for oral, topical or parenteral administration comprising a pharmaceutically acceptable carrier and a compound as claimed in claim 1 in an amount effective for the treatment of diabetes-associated chronic complications.

29. A method for treating a diabetic subject to prevent or alleviate chronic complications arising in said subject, which comprises administering to said diabetic subject an effective amount of a compound as claimed in claim 1.

* * * * *